United States Patent [19]
Charrier

[11] Patent Number: 4,741,015
[45] Date of Patent: Apr. 26, 1988

[54] UNIVERSAL X-RAY UNIT

[75] Inventor: Pierre Charrier, Montreal, Canada

[73] Assignee: B. C. Medical Compagnie Limitee, Montreal, Canada

[21] Appl. No.: 938,639

[22] Filed: Dec. 5, 1986

[51] Int. Cl.⁴ .......................... A61B 6/00; G03B 42/00
[52] U.S. Cl. ...................................... 378/196; 378/197
[58] Field of Search ............... 378/198, 197, 196, 195, 378/193, 17

[56] References Cited

U.S. PATENT DOCUMENTS

| | | |
|---|---|---|
| 377,124 | 12/1973 | Pavkovich . |
| 2,700,735 | 1/1955 | Kizaur ................................ 378/196 |
| 2,818,510 | 12/1957 | Verse .................................. 378/197 |
| 3,281,598 | 10/1966 | Hollstein ............................ 378/196 |
| 3,588,499 | 6/1971 | Pegrum . |
| 3,783,251 | 1/1974 | Pavkovich . |
| 3,803,417 | 4/1974 | Kok . |
| 3,833,813 | 6/1974 | James . |
| 4,020,348 | 4/1977 | Turcotte et al. . |
| 4,187,429 | 2/1980 | Tomita et al. ......................... 378/17 |
| 4,298,801 | 11/1981 | Heitman et al. ...................... 378/196 |
| 4,481,656 | 11/1984 | Janssen et al. . |
| 4,501,011 | 2/1985 | Hauck et al. . |

Primary Examiner—Craig E. Church
Assistant Examiner—T. N. Grigsby
Attorney, Agent, or Firm—Robic, Robic & Associates

[57] ABSTRACT

An X-ray apparatus capable of X-ray beaming in a multiplicity of directions around and through the body of a patient lying horizontally stationary on a table. The X-ray equipment is fixed to a ring which circumscribes the table and the patient. This ring is held on a support and is able to be driven into rotation, relative to the support, about its center. The apparatus also includes a fork-like suspension member which has a pair of side legs located each on one outward side of the support; the lower ends of the legs being connected with the support such as to allow the latter, and the ring it holds, to be oscillated in unison by a suitable motor mechanism about a horizontal axis joining the two lower ends of the legs; this horizontal axis being further normal to the axis of rotation of the ring. The suspension member is in turn connected to a carrier assembly provided on a top structure of the frame of the X-ray apparatus. This assembly includes a carrier on which the suspension member is centrally mounted for displacement over the patient's table as well as for rotation of the suspension member, and hence the ring and the X-ray equipment fixed on it, about a vertical axis which intersects the axes of ring rotation and oscillation.

15 Claims, 10 Drawing Sheets

UNIVERSAL X-RAY UNIT

BACKGROUND OF THE INVENTION

1. Field of the Invention

The present invention relates to an X-ray apparatus capable of beaming in a multiplicity of directions around the body of a horizontally disposed stationary patient so that a complete, three-dimensional or sectional picture of the patient's anatomy (tomography) is made available without major changes in components of the apparatus or without having to change the position of the patient.

2. Description of the Prior Art

X-raying of the above type intended to provide as complete a radiographic picture as possible of a human body are already known. These apparatus however can only solve the problem partially and further separate steps have to be taken in order to obtain a vision of all parts of the body. In other words, the known apparatus do not do a complete job. Additionally, the known devices are bulky and awkward to use which does not facilitate obtaining the desired information.

SUMMARY OF THE INVENTION

It is an object of the present invention to provide an apparatus which is appreciably improved over those of the prior art in that it is able to scan all parts of the human body without having to move the patient who may rest still horizontally on the X-raying table during the complete operation. Another object is to provide an apparatus wherein the complete operation can be carried out without changing or adding any parts. In fact, the apparatus according to the invention works as if the X-raying equipment was moving along the inner surface of a hollow sphere into which the patient's body was lying still.

In accordance with the invention, these objects are achieved with an apparatus in which the X-ray equipment is fixed to a ring which circumscribes the table and the patient. This ring is held on a support and is able to be driven into rotation, relative to the support, about its center. The apparatus also includes a fork-like suspension member which has a pair of side legs located each on one outward side of the support, the lower ends of the legs being connected with the support such as to allow the latter, and the ring it holds, to be oscillated in unison by means of a suitable motor mechanism about a horizontal axis joining the said two lower ends of the legs, this horizontal axis being further normal to the axis of rotation of the ring. The suspension member is in turn connected to a carrier assembly provided on a top structure of the frame of the X-ray apparatus, This assembly includes a carrier on which the suspension member, and hence the ring and the X-ray equipment fixed on it, are centrally and rotatably mounted for rotation about a vertical axis which intersects the axes of ring rotation and oscillation.

IN THE DRAWINGS

A description of a preferred embodiment of the invention will now be given with reference to the appended drawings, in which.

DESCRIPTION OF THE PREFERRED EMBODIMENT

Figure 1:
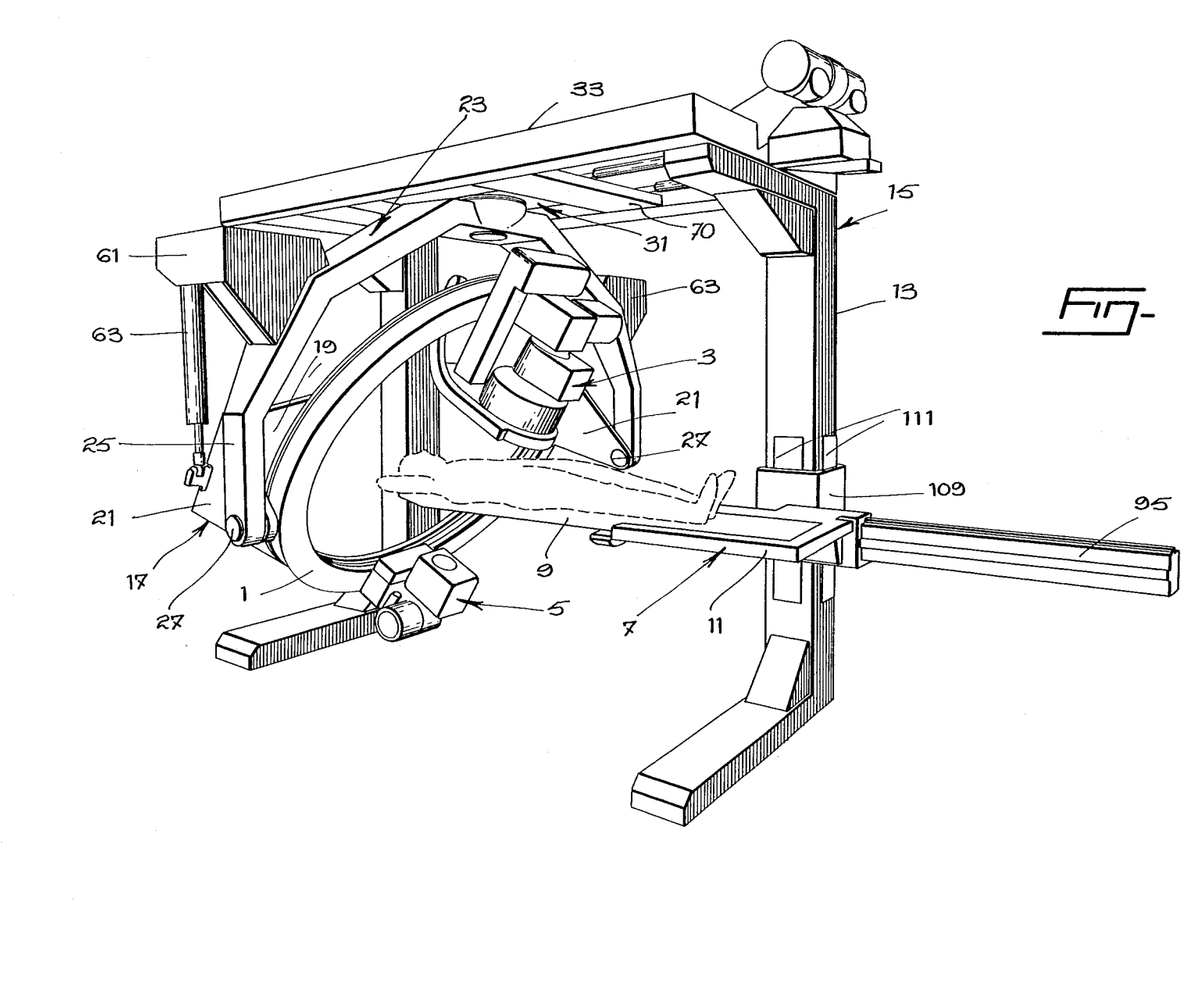
FIG. 1 is a perspective view of an X-ray apparatus made according to the invention.

The apparatus according to the invention as generally shown in FIG. 1, comprises a ring 1 at the periphery and one face of which is secured, in any known manner, a standard X-ray equipment made up of an X-ray transmitter 3 and an X-ray receiver 5, the latter being diagonally opposite to the transmitter and connected to a television circuit with the X-ray equipment then working like a television camera.

The patient lies horizontally stationary on a table 7 which, as will be seen later, can be made to move axially and vertically for the patient to be placed at various locations in the ring 1 and thus be moved with respect to the X-ray equipment. A forward portion 9 of the table 7 is made of X-ray non-absorbent material, such as plastic material, for use with the X-ray equipment and a rear portion 11 to be connected to a post 13 of a frame 15, more fully described hereinafter.

The ring 1 is mounted on a support 17 for rotation about a first axis 18 (FIGS. 6, 7) intersecting the ring center C (FIG. 2), perpendicularly of the general plane of the ring 1. The support 17 has a back plate 19 holding the ring 1 and a pair of wings 21 solid with the back plate 19 and projecting perpendicularly therefrom and from the same face as the ring 1 (FIGS. 1, 11 and 12).

The support 17 is connected to a suspension member 23, fork-like in outlook, which has a pair of downwardly extending side legs 25 of which the free ends are located on either outward side of the supports 17 and are connected thereto by first pivot means 27 to allow oscillation of the ring 1 (FIGS. 6 and 7) about a horizontal second axis 29 (FIG. 2) lying forwardly of the general plane of the ring 1 and intersecting its axis of rotation, or first axis 18, at right angles. As shown clearly in FIGS. 6 to 9, the first pivot means 27 stands away forwardly of the general plane of the ring.

Figure 4:
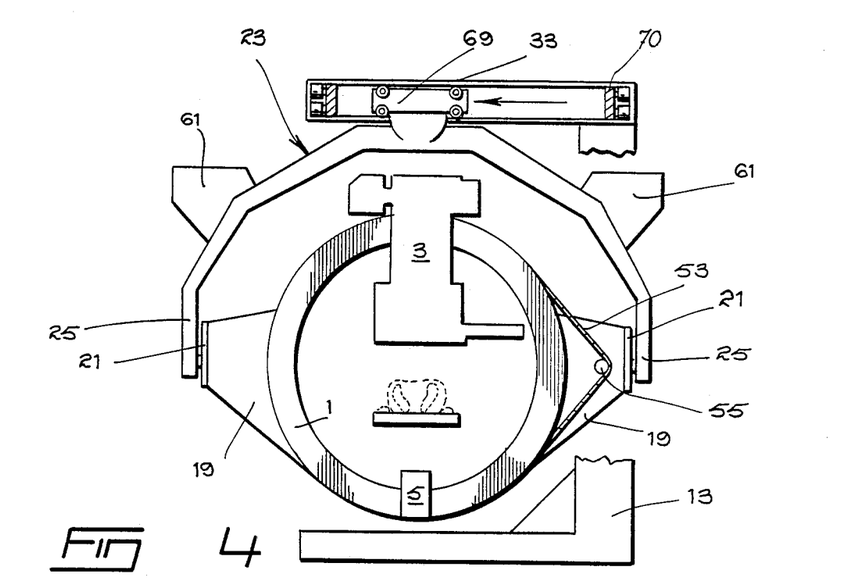
FIGS. 4 and 5 are similar to FIGS. 2 and 3 but show how the ring can move transversely of the patient's table.
Figure 5:
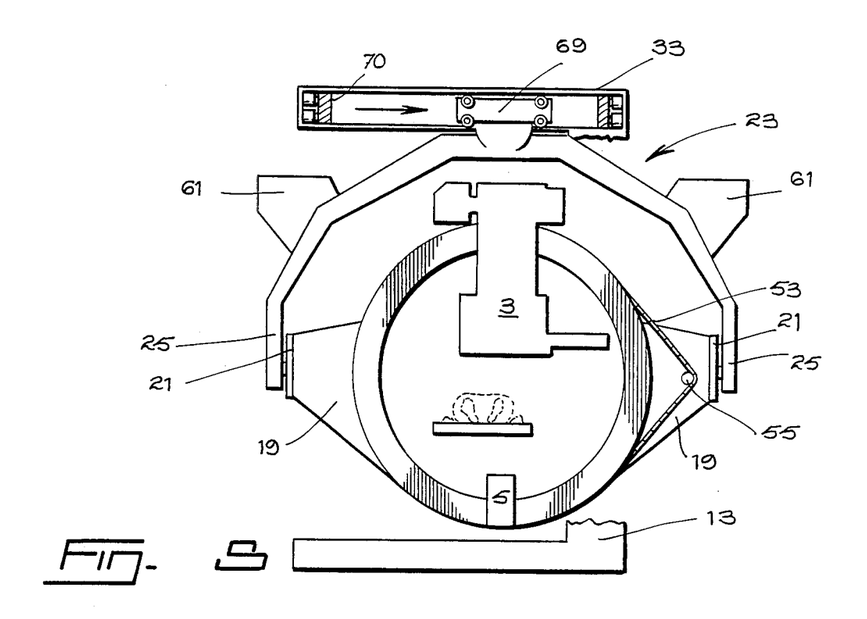
Figure 6:
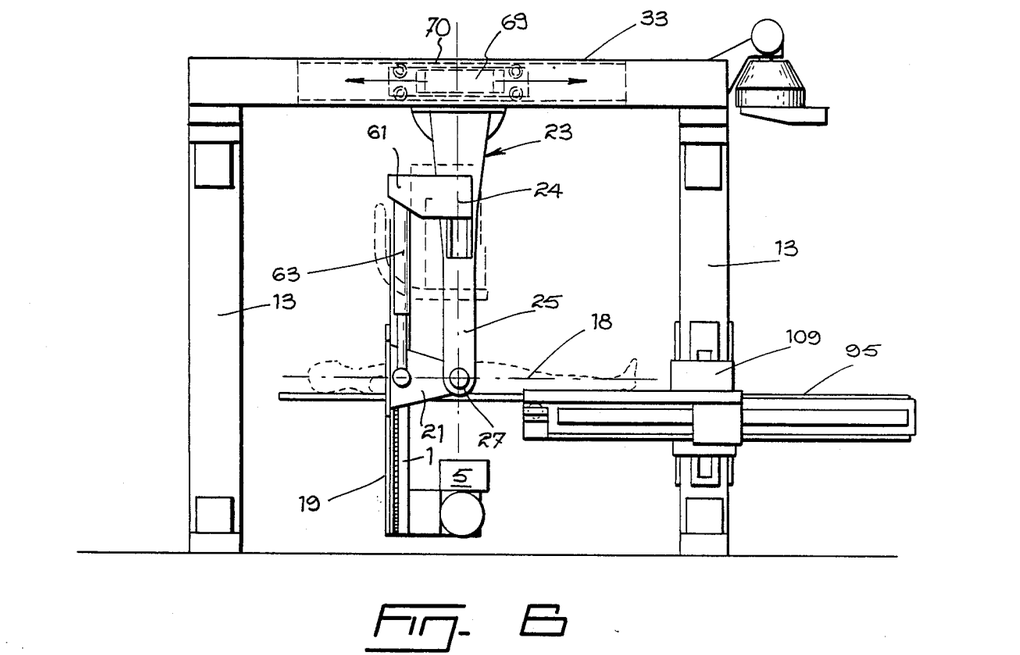
FIGS. 6 and 7 are side elevation views illustrating how the X-ray ring can swing back and forth in a vertical plane.

The suspension member 23 is, in turn, supported centrally by a carrier assembly 31 (FIGS. 1 and 13) mounted on a top structure 33 of the aforesaid frame 15. The carrier assembly 31 includes bidirectional slide means which allow the suspension member 23 (and thus the ring 1 through the supports 17) to be moved longitudinally of the table 7, as shown in FIG. 6, and transversely thereof as shown in FIGS. 4 and 5. The carrier assembly 31 further includes second pivot means which allow rotation of the suspension member 23, and thus the ring 1, about a vertical axis 24 in the manner illustrated in FIGS. 8 and 9. These slide means and second pivot means are detailed hereinafter.

Figure 11:
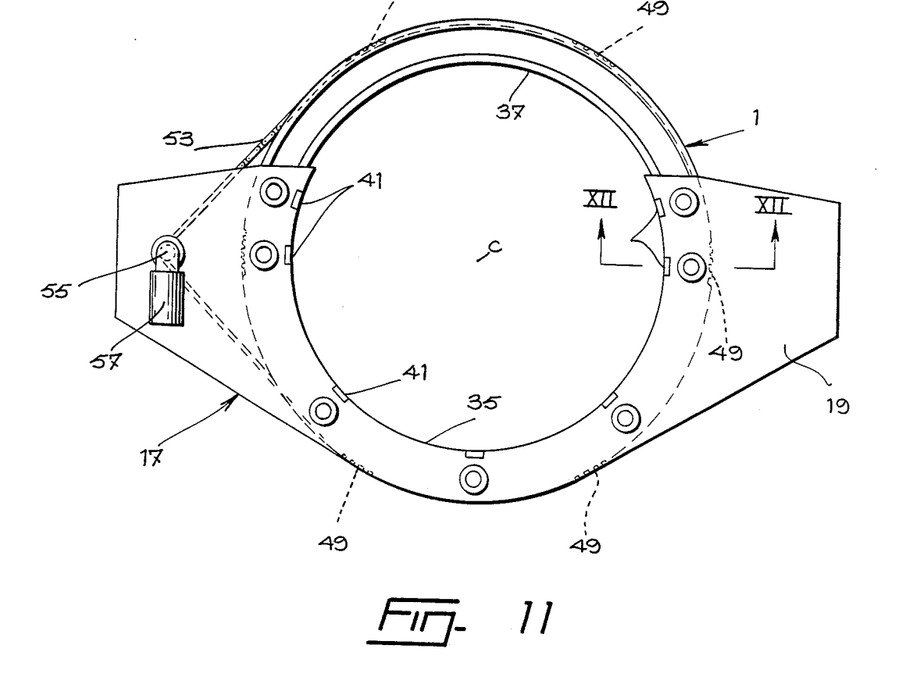
FIG. 11 is a rear elevation view of the X-ray ring and its support.
Figure 12:
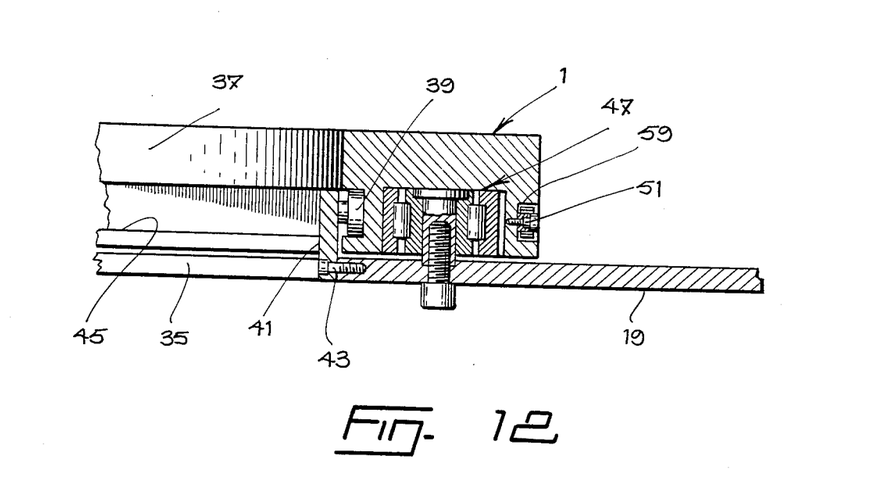
FIG. 12 being a cross-section taken along line XII—XII of FIG. 11.

Referring to FIGS. 11 and 12, it will be seen that the back plate 19 of the support 17 is formed with a central arcuate opening 35 having a diameter somewhat smaller but however essentially equal to that of the bore 37 of the ring 1. FIG. 12 shows that one face of the ring 1 lies over one face of the back plate 19; the arcuate opening 35 and the bore 37 being coaxial.

The ring 1 is mounted for rotation about the first axis 18 of rotation (FIGS. 6 and 7) intersecting the ring center C and being perpendicular to the general plane of the ring 1; the mounting being by roller means now to be broadly described and which may be of any conventional type.

Referring to FIGS. 11 and 12, the aforesaid roller means comprise a series of rollers 39 held by short arms 41 secured by screws 43 to the edge of the back plate 19 around the central opening 35; these rollers riding in a raceway 45 formed in the bore 37 of the ring 1. Additionally, standard roller bearings 47 may advantageously join the ring 1 to the plate 19, as clearly shown in FIG. 12.

As mentioned above, the ring 1 is rotated, clockwise or counterclockwise about its center C, by a first drive means which comprise toothed rack means, a drive motor and a sprocket chain. The rack means is preferably in the form of a series of short arcuate rack segments 49 fixed at the periphery of the ring 1 by screws 51 and spaced from one another. A sprocket chain 53 meshes with the rack segments 49 and with a drive sprocket 55 of an electric motor 57 fixed to the support back plate 19, as illustrated in FIG. 11. Thus, rotation of the drive pinion 55 by the motor 57 entrains the chain 53 which in turn rotates the ring 1 in either direction depending on the direction of rotation of the pinion 55.

Advantageously and as best shown in FIG. 12, the peripheral outer edge of the ring 1 may be formed with an uninterrupted groove 59 into which the rack segments 49 are housed.

As viewed from FIGS. 1, 2 and 6 to 10, oscillation of the ring 1 and its support 17 about the horizontal second axis 29 is obtained by a second drive means which comprises, on each side of the ring 1: an angled bracket 61 solid with the adjacent leg 25 of the suspension member 23 above the first pivot means 27 and projecting therefrom in the direction of the ring; an electrically actuated power jack 63 of which the free end of the axially reciprocating rod is pivoted to the adjacent wing 21 and the cylinder free end is likewise pivoted to the outer end of the bracket 61. Pivoting of the free end of the jack rods, with respect to the ring, is about an axis which lies essentially in the general plane of the ring so that the jack 63 remains vertical as clearly illustrated in FIGS. 6 and 7.

Further details of the carrier assembly 31 will now be described with reference to FIGS. 4, 5, 6, 13, 14 and 18.

As aforesaid, the assembly comprise bidirectional slide means 65 and second pivot means 67.

Figure 13:
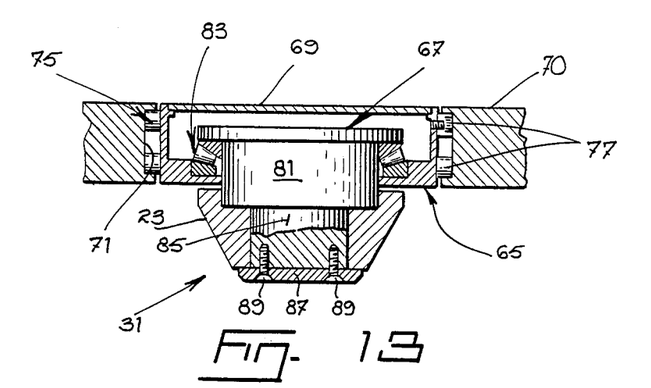
FIG. 13 is a vertical cross-section view of taken along line XIII—XIII of FIG. 18, of the carrier assembly and of the adjoining part of the frame top structure.
Figure 14:
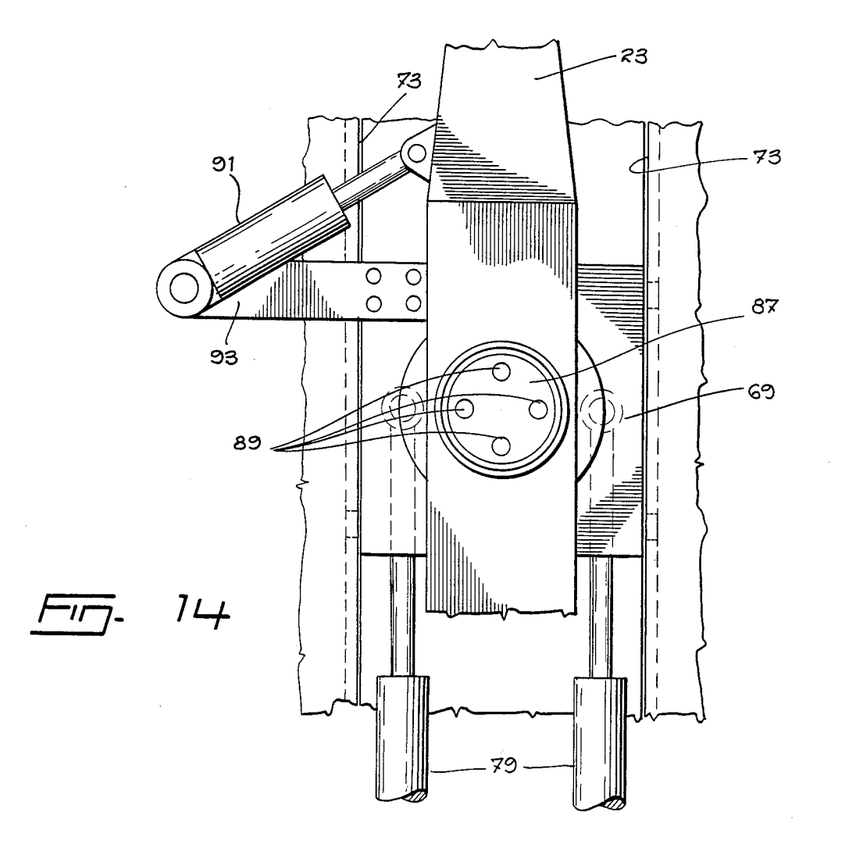
FIG. 14 is a bottom plan view of the part illustrated in FIG. 13.
Figure 18:
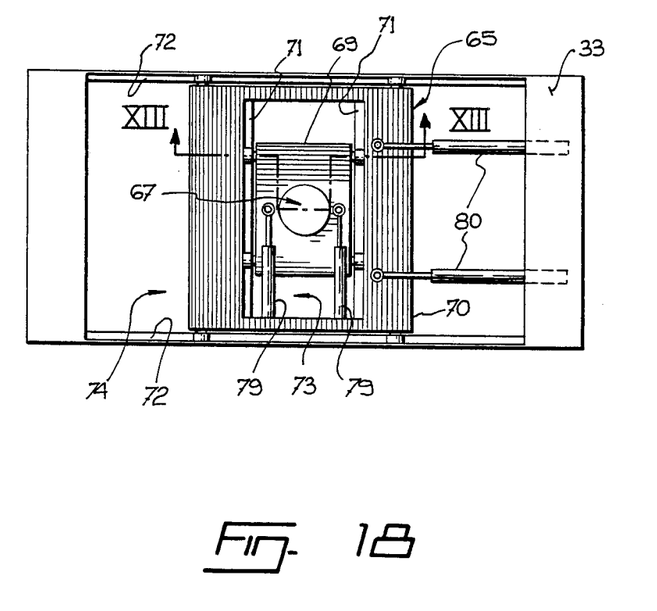
FIG. 18 is a top plan view of the carrier assembly and the adjoining parts of the frame top structure.

The slide means 65 includes a hollow carrier 69 (referred to as "second carrier" in the claims), having a releasable open top (shown in FIG. 13). The carrier 69 is displaceably mounted in a first set of roller races 71 formed along two opposite sides of an elongated opening 73 provided in a larger carrier 70 (referred to as "first carrier" in the claims). This larger carrier 70 is in turn displaceably mounted into a second set of roller races 72 perpendicular to the first one, which second set is formed along two opposite sides of an elongated opening 74 longitudinally extending in the top structure 33 (FIG. 18). Displacement is made possible in both of said openings 73 and 74 by conventional roller means.

One of said roller means 75 is shown in detail in FIG. 13. It comprises a set of rollers 77 which ride freely in the races 71. Displacement of the carrier 69, along the races 71 in the transversal direction, is achieved by means of one or preferably two parallel electrically actuated power jacks 79 shown at the bottom of FIG. 14 and in FIG. 18, of which the free ends of the cylinders are connected to the larger carrier 70 in any known manner. Similarly, displacement of the larger carrier 70 along the races 72 in the longitudinal direction is achieved by means of one or preferably two parallel electrically actuated jacks 80 shown in FIG. 18, of which the free ends of the cylinders are connected to the top structure 33.

The second pivot means 67, on the other hand, has a cylindrical pivot heat 81 mounted on the carrier 69 through conventional roller means 83 allowing the head to rotate about the aforesaid vertical axis 24 normal to the carrier 69 (FIG. 13). Solid with the head 81 is a coaxial counterpin 85. The suspension member 23 is fixed, at its center intermediate the side legs 25, to the head 81 and pin 85 by a round connector plate 87 and screws 89. Rotation of the suspension member 23 is by means of second power jack means including an electrically actuated jack 91 connected, respectively, to the suspension member 23 and to one end of a bar 93 of which the other end is screwed to the bottom of the carrier 69.

Figures 15, 16, 17:
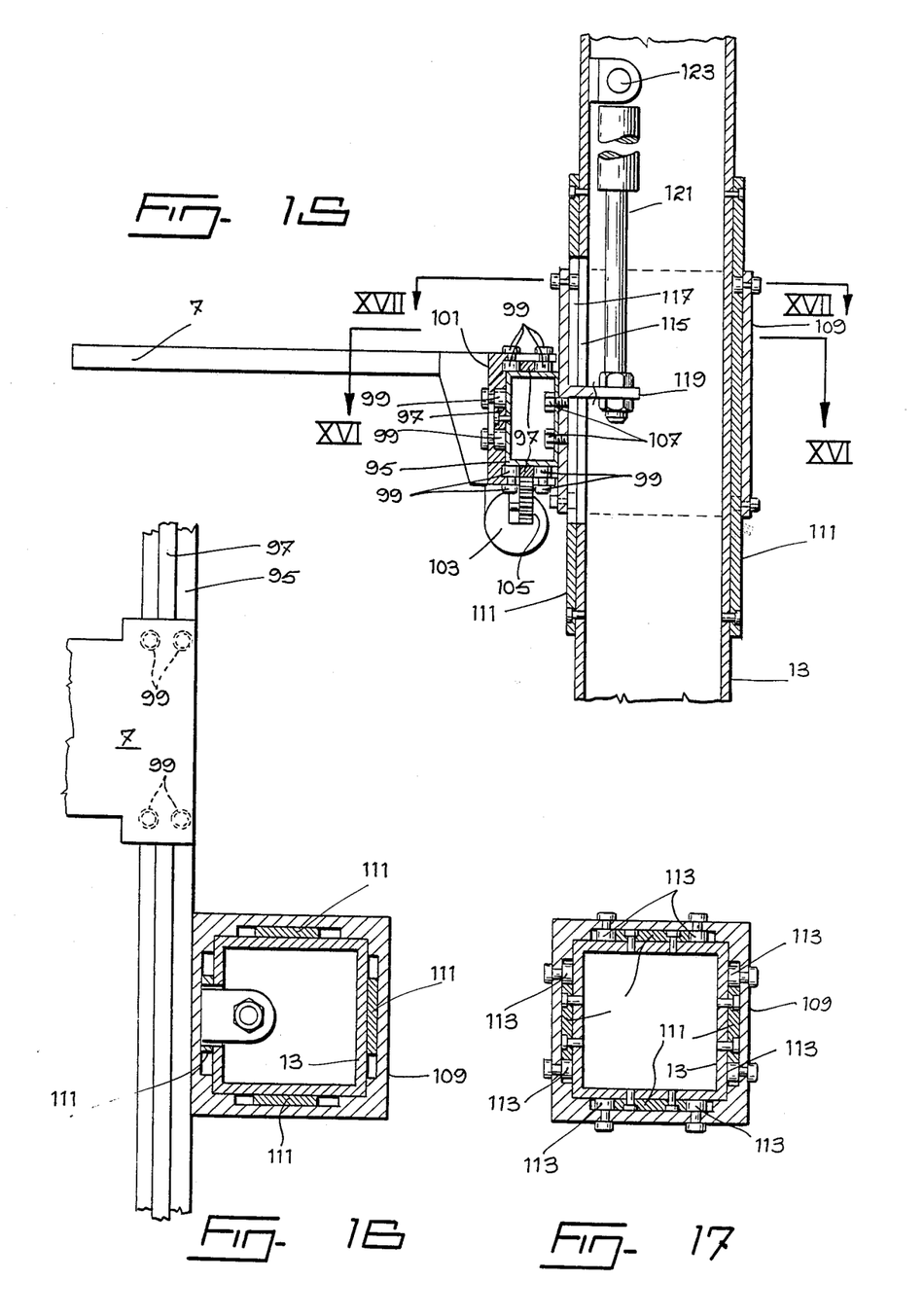
FIG. 15 is a vertical cross-sectional view taken along line XV—XV of FIG. 15, of the table supporting post in the ares of its connection to the slide rail along which the table can be displaced.
FIG. 16 is a transverse cross-sectional view taken along line XVI—XVI of FIG. 15, of the post from beneath the power jack used for lifting the table, a portion of the latter however being shown in plan view.
FIG. 17 is a further transverse cross-sectional view taken along line XVII—XVII of FIG. 15, of the post taken with the jacket having a portion thereof located above a slot of the post.

FIGS. 15, 16 and 17 show the constructional features making it possible for the table 7 to be moved both horizontally in its own plane and vertically, parallel to itself.

The means which allow the table 7 to be moved horizontally axially comprise an eleongated horizontal hollow beam 95 extending along one side of the table 7. It is provided, on three faces, with roller guiding strips 97 for the engagement of rollers 99 rotatably mounted on threee facing walls of an essentially channel-shaped profile 101 which forms part of the table 7. The channel 101, rollers 99 and strips 97 thus form roller means allowing easy displacement of the table 7 along the beam 95. Positive movement of the channel-shaped profile 101, and thus the table 7, along the hollow beam 95 is by means of an electric motor 103 having a drive pinion 105 and being secured to and beneath the channel-shaped profile 101. The drive pinion 105 meshes with a toothed rack provided at the top of the lower guiding strip 97 of the beam 95. Rotation of the pinion 105 thereby causes displacement of the table 7 along the beam 95.

The hollow beam 95 is, in turn, secured to one face of a square jacket 109 by means of screws 107; holes (not shown) being provided, for this purpose, through the wall of the hollow beam 95 opposite that through which the screws 107 are driven. The jacket 109 is able to slide along the post 13 by means best illustrated in FIGS. 16 and 17 and including guide strips 111, screwed each to one outer face of the post 13, and rollers 113 rotatably mounted on the jacket 109 to ride along two opposed lateral edges of the guide strips 111.

The post 13 and the guide strip 111 facing the table 7 are formed with registering elongated slots 115, 117 (FIG. 15). A leg 119, solid with the jacket 109, projects through these slots 115, 117, and into the hollow post 13. An electrically actuated power jack 121, interconnected between the leg 119 and a bracket 123, ensures displacement of the table 7 through the beam 95 and jacket 111, when actuated; the movement being selectively up or down depending on the direction of actuation of the jack 121.

Figure 2:
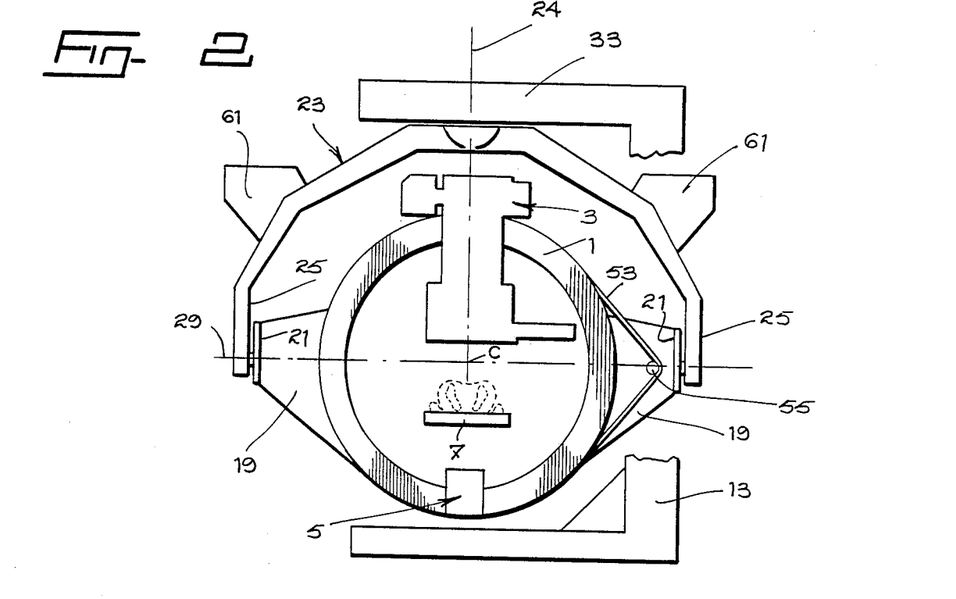
FIGS. 2 and 3 are end elevation view of the apparatus of FIG. 1 showing the rotation possibility of the ring, carrying the X-ray equipment, about its center.
Figure 3:
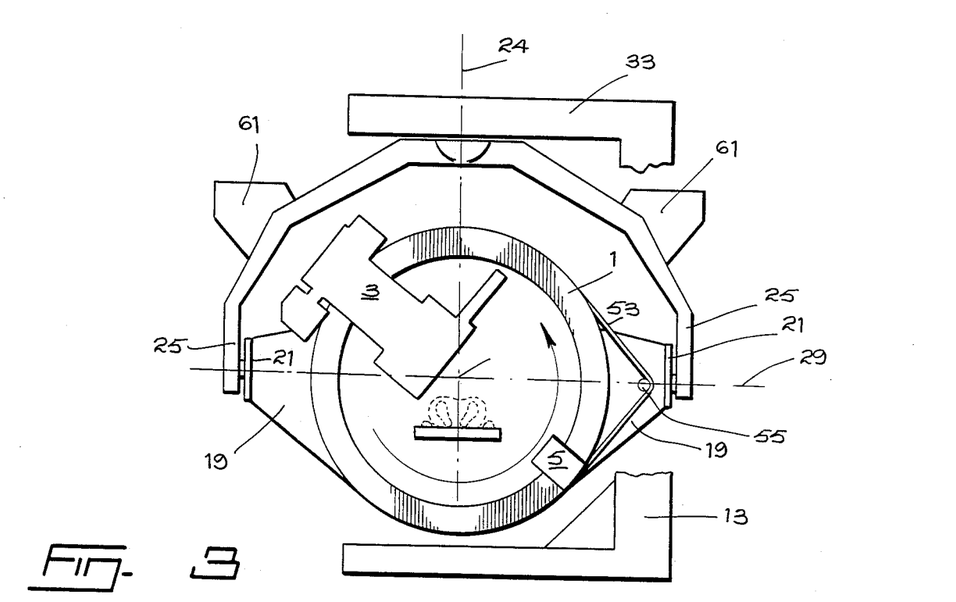

To resume, FIGS. 2 and 3 show the possibility of rotating the ring 1 and relevant X-ray equipemnt 3, 5, fully around the patient on table 7, regardless of the inclination of the ring 1 (FIGS. 6 and 7) with respect to the horizontal plane of the table or with respect to a vertical plane transverse to the table. FIGS. 4 and 5 show that it is also possible to shift the ring 1 transversely of the table even if the said ring is inclined as in FIGS. 7 or 9 even if it is vertical as in FIGS. 2 to 5. FIGS. 15, 16 and 17 illustrate that the table 7 may be moved vertically or horizontally to occupy different positions within the ring 1.

The operation of the apparatus of the invention can thus be compared to the working of the X-ray equipment 3 and 5 operating from the inner wall of a hollow sphere thereby providing full scanning of the body of a patient. Acting as a television camera, the continuous viewing under various angles, of the patient's body by the X-ray equipment may be reproduced on a TV screen to which receiver 5 may be hooked.

Figure 10:
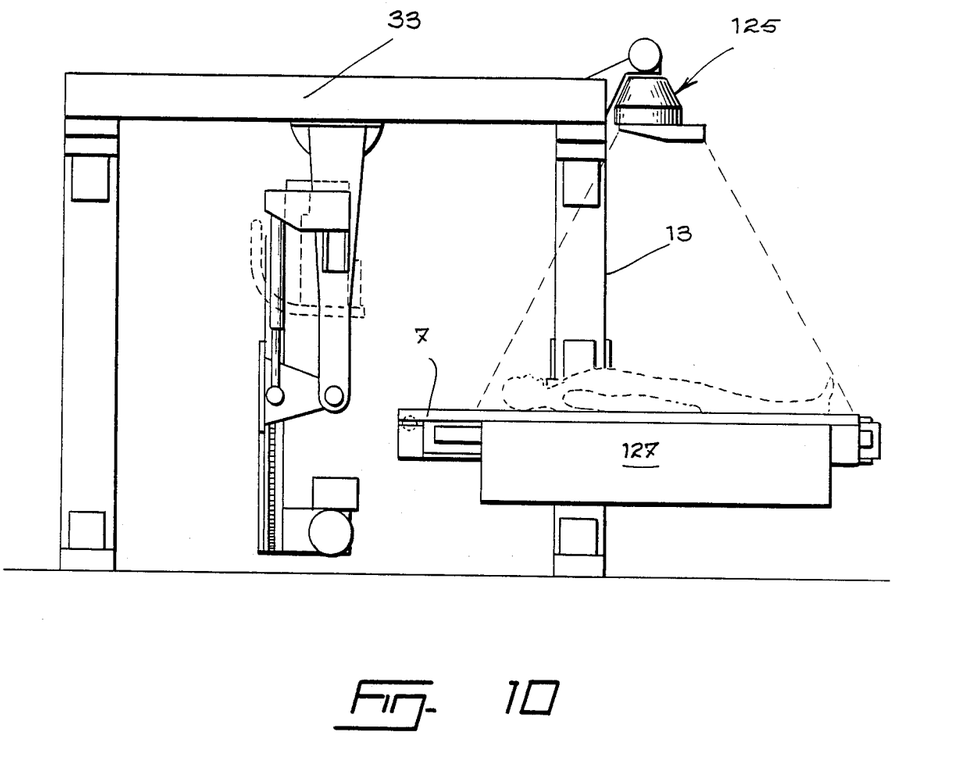
FIG. 10 is a side elevation view showing the table in position for taking radiographs from above.

Referring to FIG. 10, it may be seen that the apparatus of the invention may readily be adapted for the taking of still radiographs by having a suitable standard X-ray camera 125 mounted on the frame top surface 33 to slightly overhand therefrom. A film-carrying cassette 127 is, in this case, mounted beneath the table 7 which is of course moved below the camera 125.

Figure 7:
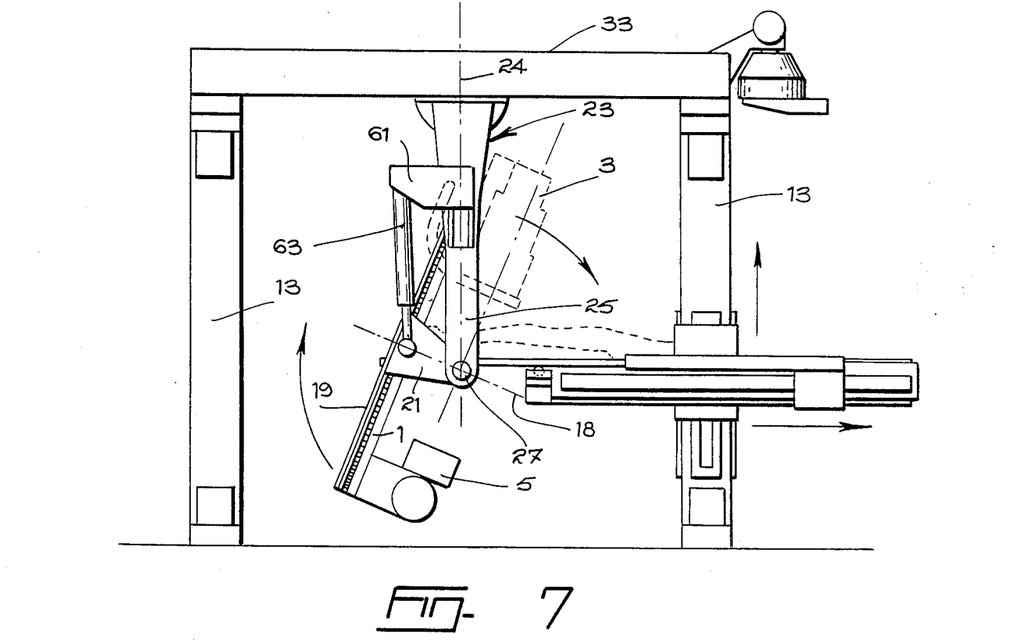
Figure 8:
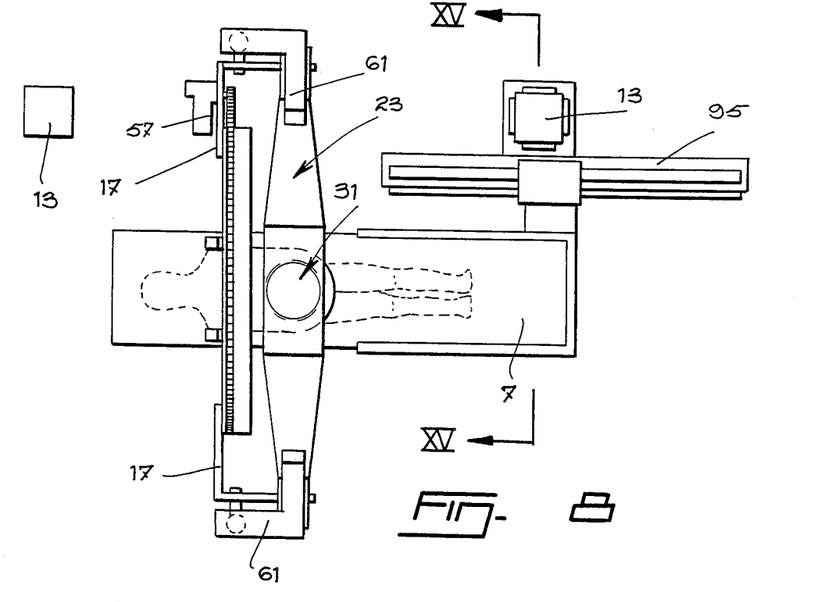
FIGS. 8 and 9 are top views illustrating how the X-ray ring can be made to rotate about a vertical axis.
Figure 9:
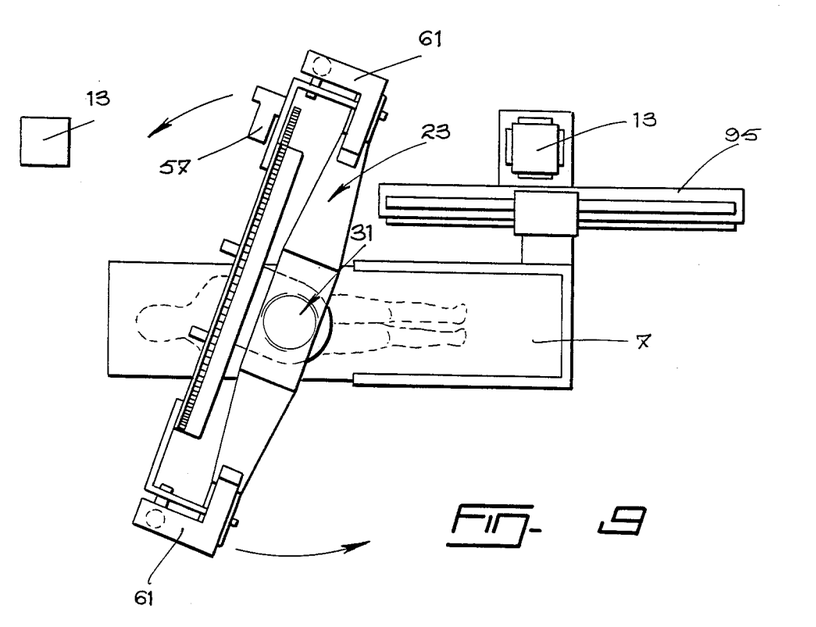

Finally, referring to FIG. 7, it is noted that the X-ray beam 129 emitted by the tramsitter 3 intersects, at all times, the point of intersection of the horizontal oscillation axis 29 (FIG. 2), the vertical pivot axis 24 and the rotation axis of 18 of the ring 1.

I claim:

1. An X-ray appartus capable of X-ray beaming in a multiplicity of directions around and through the body of a horizontally lying stationary patient, said apparatus comprising:
   a horizontal patient's table;
   a ring in circumbscribing position around said table, said ring having a center;
   a X-ray equipment fixedly mounted on said ring for X-ray beaming through said table and through the body of a patient when lying thereon, said X-ray equipemnt comprising a source of X-rays;
   support means for holding said ring in said circumscribing position and first drive means on said support means and on said ring for rotating said ring about a first axis perpendicular to the general plane of said ring and through said ring center;
   a suspension member having downwardly extending side legs, located one either side of said support means, and first pivot means at the lower ends of said side legs and on said support means for allowing oscillation of said ring about a second axis intersecting said first axis at right angles;
   second drive means for oscillating said ring support means and said ring together in unison about said second axis;
   a frame having a top structure above said table, said ring and said suspension member; and
   a carrier assembly mounted on said top structure and at the center of said suspension member, intermediate said side legs, for supporting said suspension member; said carrier assembly including second pivot means for rotating said suspension member, support means and ring, about a vertical axis extending perpendicularly through said suspension number, centrally thereof intermediate said legs; said vertical axis intersecting said first and second axes.

2. An apparatus as claimed in claim 1, further comprising means on said table and on said frame for moving said table horizontally and vertically.

3. An apparatus as claimed in claim 1, wherein said ring support means comprises: a back plate formed with a central arcuate opening having a diameter essentially equal to the inner diameter of said ring, one face of said ring lying over one face of said back plate along said arcuate opening; and roller means on said back plate and on said ring allowing rotation of said ring with respect to said back plate and about said first axis; said arcuate opening of said back plate being thus coaxial with said ring.

4. An apparatus as claimed in claim 3, wherein said first drive means comprise: toothed rack means at the periphery of said ring; a drive motor on said one face of said back plate, said motor including a drive pinion; and a sprocket chain meshing with said toothed rack means and with said pinion for driving said ring into rotation with respect to said back plate.

5. An apparatus as claimed in claim 4, wherein said ring is formed with an outwardly open uninterrupted groove at the periphery thereof and said toothed rack means are mounted in said groove.

6. An apparatus as claimed in claim 5, wherein said toothed rack means comprise a plurality of arcuate toothed rack segments spacedly mounted in said peripheral groove.

7. An apparatus as claimed in claim 3, wherein said ring support means further comprises: a pair of wings solid with and projecting perpendicularly from said one face of said back plate, each on one side of said ring; and wherein said first pivot means are located at the ends of said wings away from said back plate one face such that said ring stands away from and is parallel to said second axis.

8. An apparatus as claimed in claim 7, wherein said second drive means comprise, on each side of said ring:
   a bracket solid with one of said legs of said suspension member above said first pivot means and projecting therefrom in the direction of said ring; a power jack having one end pivoted to the free end of said bracket and having the other end pivoted to an adjacent one of said wings for pivotal movement of said one end of said jack with respect to said ring, about an axis lying essentially in said general plane of said ring.

9. An apparatus as claimed in claim 1, wherein said top structure of said frame has an elongated opening therethrough and said carrier assembly further includes slide means for allowing said suspension member, support means and ring to be moved longitudinally and transversely within said elongated opening, said slide means comprising:
   a first carrier mounted in said elongated opening and provided with a central opening;
   first roller means on said first carrier and cooperating with said top structure, along opposed faces of said opening, suitable to allow movement of said first carrier in a first direction with respect to said top structure and to said table;
   a second carrier mounted in said central opening of the first carrier; and
   second roller means on said second carrier along opposed faces of said central opening cooperating with said first carrier, suitable to allow movement of said second carrier with respect to the first one and to said table in a second direction perpendicular to the first one; wherein said second pivot means of said carrier assembly comprise:
   a pivot head and roller means mounting said pivot head on said second carrier for rotation thereof about said vertical axis extending perpendicularly through said suspension member, and
   means securing said suspension member to said pivot head to be rotated thereby. and wherein said carrier assembly further comprise:
   first power jack means for moving said first carrier;
   second power jack means for moving said second carrier; and
   third power jack means causing rotation of said pivot heat and suspension member secured thereto.

10. An apparatus as claimed in claim 2, wherein said means for moving said table horizontally comprise:
    an elongated horizontal extending along one side of said table;
    roller means interconnecting said beam and said one side of said table for allowing horizontal displacement of said table along said beam; and
    actuating means on said table and on said beam suitable to allow said horizontal displacement of said table, and wherein said means for moving said table vertically comprise:
    a hollow vertical post as part of said frame, said post having an elongated vertical through slot;
    jacket means around said post including a jacket slidable vertically along said post and formed with an elongated vertical through slot registering with said post through slot;
    a leg solid with said jacket, extending through said registering slots and projecting inside said hollow post;
    means securing said elongated horizontal beam to said jacket, and
    power jack means within said hollow post, fixed at one end to said post and, at the other end, to said leg for moving said jacket vertically thereby moving said table vertically through said beam secured to said jacket.

11. An apparatus as claimed in claim 10, further comprising:
    another X-ray equipment for taking radiographs;
    means for mounting said other X-ray equipment on said top sturcture of said frame to overhang from said vertical post and to transmit an X-ray beam over said table; and
    an X-ray sensitive film in said table for absorption of X-rays from said other X-ray equipment when said table, with said film therein, is moved beneath said other X-ray equipment.

12. An apparatus as claimed in claim 1, wherein said X-ray equipment comprises:
    a transmitter for tranmitting X-rays, and
    a receiver, positioned diametrically opposite said transmitter on said ring, for picking up said transmitted X-rays; said X-ray equipment being positioned for transmitting a beam extending in a plane including said second axis and the point of intersection of all of said axes.

13. An apparatus as claimed in claim 7, wherein said X-ray equipment comprises:
    a transmittter for transmitting X-rays, and
    a receiver, positioned diametrically opposite said transmitter on said ring, for picking up said transmitted X-rays; said X-ray equipment being positioned for transmitting a beam extending in a plane including said second axis and the point of intersection of all of said axes.

14. An apparatus as claimed in claim 9, wherein said X-ray equipment comprises:
    a transmitter for transmitting X-rays, and
    a receiver, positioned diametrically opposite said transmitter on said ring, for picking up said transmitted X-rays; said X-ray equipment being positioned for transmitting a beam extending in a plane including said second axis and the point of intersection of all of said axes.

15. An apparatus as claimed in claim 10, wherein said X-ray equipment comprises:
    a transmitter of transmitting X-rays, and
    a receiver, positioned diametrically opposite said transmitter on said ring, for picking up said transmitted X-rays; said X-ray equipment being positioned for transmitting a beam extending in a plane including said second axis and the point of intersection of all of said axes.

* * * * *